United States Patent
Windecker et al.

(10) Patent No.: US 7,598,405 B2
(45) Date of Patent: Oct. 6, 2009

(54) METHOD FOR THE DISTILLATIVE PROCESSING OF TETRAHYDROFURAN

(75) Inventors: Gunther Windecker, Ludwigshafen (DE); Alexander Weck, Freinsheim (DE); Markus Roesch, Dienheim (DE); Michael Steiniger, Neustadt (DE); Rolf Pinkos, Bad Duerkheim (DE); Dany Vanden Hautte, Bernissart (BE)

(73) Assignee: BASF Aktiengesellschaft, Ludwigshafen (DE)

( * ) Notice: Subject to any disclaimer, the term of this patent is extended or adjusted under 35 U.S.C. 154(b) by 209 days.

(21) Appl. No.: 11/575,668

(22) PCT Filed: Sep. 21, 2005

(86) PCT No.: PCT/EP2005/010186

§ 371 (c)(1),
(2), (4) Date: Mar. 21, 2007

(87) PCT Pub. No.: WO2006/034805

PCT Pub. Date: Apr. 6, 2006

(65) Prior Publication Data

US 2008/0058539 A1  Mar. 6, 2008

(30) Foreign Application Priority Data

Sep. 29, 2004 (DE) .................. 10 2004 047 201

(51) Int. Cl.
*C07D 307/02* (2006.01)
*B01D 3/34* (2006.01)
*B01D 3/00* (2006.01)
(52) U.S. Cl. .................. 549/509; 203/50; 203/71
(58) Field of Classification Search .................. 203/50, 203/71

See application file for complete search history.

(56) References Cited

U.S. PATENT DOCUMENTS 4,175,009 A * 11/1979 Copelin .................. 203/96
5,310,954 A * 5/1994 Hiles et al. .................. 549/429

FOREIGN PATENT DOCUMENTS

| DE | 29 30 144 | 2/1981 |
| DE | 37 26 805 | 2/1989 |
| EP | 0 011 244 | 5/1980 |
| EP | 0 382 384 | 8/1990 |
| JP | 2 639 463 | 8/1997 |
| WO | 91/01981 | 2/1991 |

* cited by examiner

*Primary Examiner*—D. Margaret Seaman
*Assistant Examiner*—Nizal S Chandrakumar
(74) *Attorney, Agent, or Firm*—Oblon, Spivak, McClelland, Maier & Neustadt, L.L.P.

(57) ABSTRACT

The present invention provides a process for distillatively purifying tetrahydrofuran in the presence of a polar solvent.

11 Claims, 1 Drawing Sheet

METHOD FOR THE DISTILLATIVE PROCESSING OF TETRAHYDROFURAN

DESCRIPTION

Figure 1:
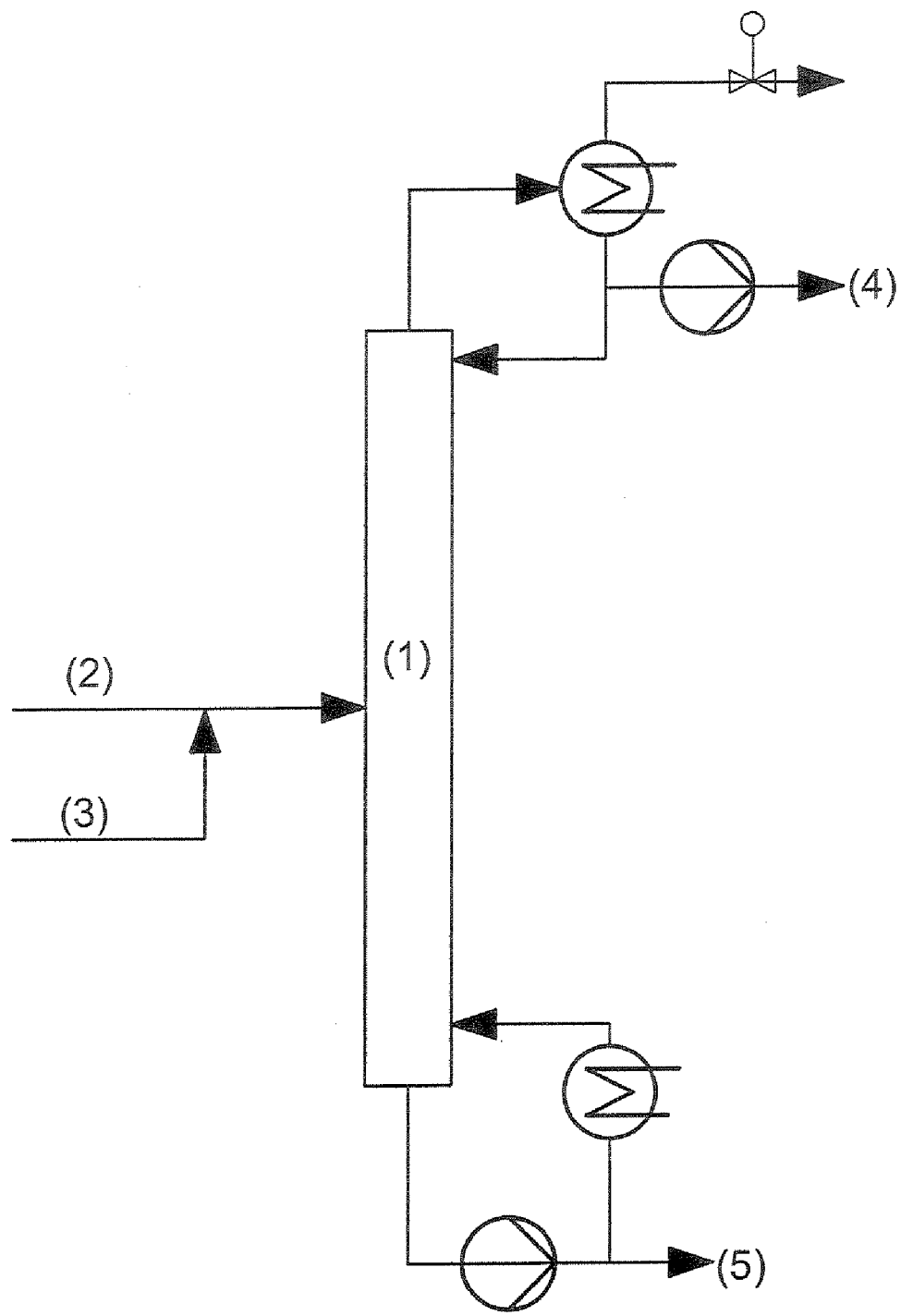

The invention relates to a process for distillatively purifying tetrahydrofuran (THF) in the presence of a polar solvent.

The preparation of THF by dehydration of 1,4-butanediol over acidic catalysts is described, for example, in DE-A 29 30 144 and leads to crude THF production with water contents of from 18 to 28% by weight and contents of up to 5% by weight of impurities caused by the synthesis, such as 2,3-dihydrofuran, 2- and 3-methyl-tetrahydrofuran.

For the recovery of pure THF from such crude products, DE-A 37 26 805 discloses a process for distillatively purifying crude aqueous THF in which the THF is passed through three distillation columns, wherein a side draw of the first column is passed into the second, the top product of the third column is recycled into the first, distillate is withdrawn at the top of the first column and the pure THF is obtained from the side draw of the third column.

The preparation of THF by gas phase hydrogenation of maleic anhydride (MA) is a reaction which has been known for many years and is described, for example, in JP-B 2639463 and JP-B 2639464. The resulting aqueous crude products differ from those obtained from butanediol dehydration especially by their higher proportion of components whose boiling point differs only slightly from the boiling point of THF, known as narrow-boiling components. The narrow-boiling components of THF are in particular methanol, ethanol and butyraldehyde, butyl methyl ether, and the azeotropes thereof with THF and/or water.

The extent to which the distillation processes known from the prior art lower the butyl methyl ether content of the aqueous crude THF products of the gas phase hydrogenation of MA or MA derivatives, or of the THF-containing recycle streams of other processes such as polytetrahydrofuran preparation, is not sufficient to be able to fulfill the purity requirements made on THF especially in the further processing of the THF, for example to give polytetrahydrofuran.

It is therefore an object of the invention to find an improved process which enables in an economically viable manner the recovery of THF with small amounts of butyl methyl ether contents from THF. It should be possible irrespective of the preparation method of the THF to achieve these purities.

This object is achieved by a process for distillatively purifying tetrahydrofuran in the presence of a polar solvent which is preferably added before the start of the distillation.

The process according to the invention can be applied to THF which has been obtained by a wide variety of preparative processes and optional subsequent purification of the resulting crude product, for example by the process known from DE-A 3726805. In the context of this application, THF refers generally to THF which has a THF content of >99% by weight, up to 1% by weight of butyl methyl ether and less than 200 ppm of further oxygen-functionalized CH compounds resulting from the preparation. Preference is given to using the process according to the invention for distillatively separating tetrahydrofuran as obtained in tetrahydrofuran synthesis by catalytic hydrogenation of maleic acid (MA) or maleic acid derivatives (MA derivatives). Maleic acid derivatives mean maleic anhydride, fumaric acid, maleic mono- and diesters, fumaric mono- and diesters, succinic acid, succinic mono- and diesters, and gamma-butyrolactone, but also maleic acid itself. The maleic acid derivatives mentioned may be catalytically hydrogenated alone or as mixtures, in solvents such as water or alcohols, in the liquid phase or in the gas phase. In addition to tetrahydrofuran, the hydrogenation effluents may comprise, inter alia, 1,4-butanediol, gamma-butyrolactone, alcohols such as methanol, ethanol, propanol, butanol, water, and unconverted maleic acid derivatives. It enables a pure THF in which the butyl methyl ether content has been distinctly lowered to be obtained.

The distillation of THF is generally carried out in the presence of an amount of from 0.1 to 100% by weight, based on the amount of THF, preferably from 0.1 to 10% by weight, more preferably from 0.1 to 2% by weight, of the polar solvent which is preferably added before the start of the distillation.

The polar solvents used may be $C_1$- to $C_{10}$-alkanols. Particular preference is given to using methanol as the polar solvent.

The polar solvent may be added undiluted or as a mixture with water. Preference is given to adding the polar solvent as an aqueous solution, in which case the content of the polar solvent in the water should be from 0.1 to 99.99% by weight, preferably from 99 to 99.99% by weight.

The distillation may be carried out in one of a plurality of stages, for example in one or more distillation stages, for example in a multistage distillation column in countercurrent, in which case it is possible to work continuously or batchwise. Preference is given to carrying out the distillation in two or more distillation stages in separating apparatus, for example columns having a plurality of plates, for example rectification columns, columns having random packing, bubble-cap tray columns or columns having structured packing.

Particular preference is given to carrying out the distillation continuously or batchwise in a distillation column operated in countercurrent, especially preferably in a multistage column having structured packing with from 1 to 100 plates, preferably 60 theoretical plates.

Useful structured packing materials are all customary column packings. However, preference is given to using fabric packings.

The butyl methyl ether is distilled out of the pure tetrahydrofuran product at pressures of from 0 to 100 bar, preferably from 0 to 20 bar, more preferably from 0 to 5 bar, at temperatures of from 10 to 320° C.

The process according to the invention will now be illustrated in detail in the examples which follow.

EXAMPLE 1

The distillation apparatus shown by FIG. 1 was used. The column (1) has 60 theoretical plates and was operated at 2 bar absolute.

A THF mixture consisting of 99.9% by weight of THF, 86 ppm of water, 24 ppm of MeOH and 654 ppm of butyl methyl ether was conducted via the feed (2) into the column. The remainder up to 100% by weight is formed by further O-functionalized CH compounds.

At the same time, 0.65% by weight methanol, based on the THF mixture from feed (2), in the form of a methanol/water mixture which contained 100 ppm of water was added via the feed (3) to the column feed (2). The feed was mounted in the middle third of the column.

The column (1) was operated with top draw (4) and bottom draw (5). The reflux ratio based on the feed stream was 2.50 (wt./wt.). From the bottom draw (5), purified THF was removed.

As the top draw (4), somewhat more than 1.6% of the feed amount was withdrawn. The top draw had a THF concentration of 59.1 by weight of THF, 39.2% by weight of MeOH, and 1.65% by weight of butyl methyl ether, and small amounts of residual water.

The THF obtained via the bottom draw (5) had 99.94% by weight of THF, 25 ppm of MeOH, and only 379 ppm of butyl methyl ether.

COMPARATIVE EXAMPLE

The column described in example 1 was operated under the same conditions. However, the methanol/water feed stream (3) was shut down, so that no methanol was supplied.

At the same feed rate and a reflux ratio of 2.50 (wt./wt.) based on the feed stream, the following result was obtained:

The THF obtained via the bottom draw (5) had 99.92% by weight of THF and 659 ppm of butyl methyl ether. The content of butyl methyl ether has actually risen slightly compared to the starting mixture.

The table which follows clearly shows the advantage of the entraining agent addition for the depletion of butyl methyl ether:

|  | $THF^1$ [% by wt.] | $BME^2$ [ppm] | $MeOH^3$ [ppm] | BME depletion [%] |
| --- | --- | --- | --- | --- |
| Feed mixture (2) | 99.9 | 654 | 24 |  |
| Example 1 | 99.94 | 379 | 25 | −42 |
| Comparative example | 99.92 | 659 | 0 | +0.8 |

$^1$THF = Tetrahydrofuran
$^2$BME = Butyl methyl ether
$^3$MeOH = Methanol

What is claimed is:

1. A process for reducing a butyl methyl ether content of tetrahydrofuran comprising:
    adding methanol to a tetrahydrofuran feed stream comprising butyl methyl ether to form a THF mixture;
    distilling the THF mixture in one or more distillation stages in a single separating apparatus;
    removing a top draw from an upper portion of the separating apparatus; and
    removing bottom draw from a lower portion of the separating apparatus; wherein
    a content of butyl methyl ether in % by weight in the top draw is greater than the content of butyl methyl ether in the THF mixture, and
    a content of butyl methyl ether in % by weight in the bottom draw is less than the butyl methyl ether content in the tetrahydrofuran feed stream.

2. The process according to claim 1, wherein the distilling comprises two or more distillation stages in the single separating apparatus.

3. The process according to claim 1, wherein the separating apparatus is a column having a plurality of plates selected from the group consisting of a rectification column, a column having random packing, a bubble-cap tray column and a column having structured packing.

4. The process according to claim 1, wherein the distilling is a countercurrent distillation.

5. The process according to claim 1, wherein a pressure in the single separating apparatus is in the range from 0 to 100 bar.

6. The process according to claim 1, wherein a temperature in the single separating apparatus is in the range from 10 to 320° C.

7. The process according to claim 3, wherein the separating apparatus is a column having structured packing, wherein the structured packing is a fabric packing.

8. The process according to claim 1, wherein an amount of methanol added to the tetrahydrofuran feed stream is from 0.1 to 100% by weight of the tetrahydrofuran in the tetrahydrofuran feed stream.

9. The process according to claim 8, wherein the methanol is added as an aqueous mixture.

10. The process according to claim 9, wherein a content of the methanol in the aqueous mixture is 0.1 to 99.99% by weight.

11. The process according to claim 1, wherein the process is continuous or batchwise.

* * * * *